United States Patent
Spångberg et al.

(10) Patent No.: US 11,621,086 B2
(45) Date of Patent: Apr. 4, 2023

(54) CUSTOMIZATION OF INDIVIDUALIZED IMPLANT

(71) Applicant: EPISURF IP-MANAGEMENT AB, Stockholm (SE)

(72) Inventors: Jeanette Spångberg, Skogås (SE); Felicia Aldrin Bernhardt, Hägersten (SE); Katarina Flodström, Danderyd (SE)

(73) Assignee: Episurf IP-Management AB, Stockholm (SE)

( * ) Notice: Subject to any disclaimer, the term of this patent is extended or adjusted under 35 U.S.C. 154(b) by 393 days.

(21) Appl. No.: 16/893,079

(22) Filed: Jun. 4, 2020

(65) Prior Publication Data
US 2021/0383931 A1    Dec. 9, 2021

(51) Int. Cl.
*G16H 50/50* (2018.01)
*G16H 30/20* (2018.01)
(Continued)

(52) U.S. Cl.
CPC ......... *G16H 50/50* (2018.01); *A61F 2/30942* (2013.01); *G06F 3/04815* (2013.01);
(Continued)

(58) Field of Classification Search
CPC ........ G16H 20/40; G16H 30/20; G16H 30/40; G16H 50/20; G16H 50/50; A61F 2/30756;
(Continued)

(56) References Cited

U.S. PATENT DOCUMENTS

| 7,468,075 B2 | 12/2008 | Lang et al. |
| 7,664,297 B2 | 2/2010 | Harada et al. |

(Continued)

FOREIGN PATENT DOCUMENTS

| CN | 108366770 A | 8/2018 |
| DE | 112016005277 T5 | 9/2018 |

(Continued)

OTHER PUBLICATIONS

Notice of Swedish Search Report from Swedish patent application No. 2050651-5, dated Feb. 4, 2021.
(Continued)

*Primary Examiner* — Nay A Maung
*Assistant Examiner* — Jose M Torres
(74) *Attorney, Agent, or Firm* — Faegre Drinker Biddle & Reath LLP

(57) ABSTRACT

In accordance with one or more embodiments herein, a system 100 for customizing an implant is provided. The system 100 comprises a processor configured to: i) obtain one or more medical image stacks of a joint; ii) obtain a three-dimensional image representation of the joint based on at least one of said medical image stacks; iii) determine damage to the joint by analyzing said medical image stacks; iv) select an implant template from a predefined set of implant templates having predetermined types and sizes; v) generate a 3D model, in which the marked damage is visualized together with the selected implant template in a proposed position; vi) display the 3D model; vii) receive an approval for said selected implant template in said proposed position; and viii) determine the final shape and dimensions of a customized implant based on said selected implant template and said proposed position.

20 Claims, 10 Drawing Sheets

(51) Int. Cl.
| | |
|---|---|
| *G16H 30/40* | (2018.01) |
| *G16H 50/20* | (2018.01) |
| *G06F 21/30* | (2013.01) |
| *G06F 30/10* | (2020.01) |
| *G06T 7/00* | (2017.01) |
| *G06T 19/20* | (2011.01) |
| *G06F 3/04815* | (2022.01) |
| *A61F 2/30* | (2006.01) |
| *G06Q 50/04* | (2012.01) |
| *G06F 111/16* | (2020.01) |

(52) U.S. Cl.
CPC .............. *G06F 21/30* (2013.01); *G06F 30/10* (2020.01); *G06T 7/0012* (2013.01); *G06T 19/20* (2013.01); *G16H 30/20* (2018.01); *G16H 30/40* (2018.01); *G16H 50/20* (2018.01); *A61F 2002/30952* (2013.01); *A61F 2002/30963* (2013.01); *G06F 2111/16* (2020.01); *G06Q 50/04* (2013.01); *G06T 2200/24* (2013.01); *G06T 2207/30008* (2013.01); *G06T 2210/41* (2013.01)

(58) Field of Classification Search
CPC .. A61F 2/30942; A61F 2/3859; A61F 2/3877; A61F 2/389; A61F 2002/30952; A61F 2002/30963; G06F 3/04815; G06F 3/04845; G06F 21/30; G06F 21/62; G06F 30/10; G06F 2111/16; G06F 2221/2113; G06T 7/0012; G06T 19/20; G06T 2200/24; G06T 2207/30008; G06T 2210/41; G06Q 50/04; Y02P 90/30; H04L 63/105
See application file for complete search history.

(56) References Cited

U.S. PATENT DOCUMENTS

| | | |
|---|---|---|
| 2005/0102315 A1 | 5/2005 | Krishnan |
| 2008/0232658 A1 | 9/2008 | Sugaya et al. |
| 2009/0268956 A1 | 10/2009 | Wiley |
| 2009/0270868 A1 | 10/2009 | Park et al. |
| 2010/0111837 A1 | 5/2010 | Boyden et al. |
| 2011/0087465 A1 | 4/2011 | Mahfouz |
| 2011/0125003 A1 | 5/2011 | Reach |
| 2011/0282473 A1 | 11/2011 | Pavlovskaia et al. |
| 2012/0265496 A1 | 10/2012 | Mahfouz |
| 2012/0310399 A1 | 12/2012 | Metzger |
| 2013/0035561 A1 | 2/2013 | Sharkey et al. |
| 2013/0110252 A1 | 5/2013 | Bake et al. |
| 2013/0137962 A1 | 5/2013 | Urish et al. |
| 2013/0211232 A1 | 8/2013 | Murphy et al. |
| 2013/0336553 A1 | 12/2013 | Buisseret et al. |
| 2014/0039454 A1 | 2/2014 | Sharkey |
| 2014/0081659 A1 | 3/2014 | Nawana et al. |
| 2014/0142643 A1 | 5/2014 | Bake et al. |
| 2014/0303990 A1* | 10/2014 | Schoenefeld .......... G16H 15/00 705/2 |
| 2015/0178447 A1* | 6/2015 | Cohen .................... G16H 30/20 705/2 |
| 2015/0260819 A1 | 9/2015 | Lauer et al. |
| 2016/0335776 A1 | 11/2016 | Maes et al. |
| 2016/0364862 A1 | 12/2016 | Reicher et al. |
| 2017/0100253 A1 | 4/2017 | Bake et al. |
| 2017/0172747 A1 | 6/2017 | Bake et al. |
| 2017/0270665 A1 | 9/2017 | Le et al. |
| 2018/0177600 A1 | 6/2018 | Karlsson et al. |
| 2018/0253847 A1 | 9/2018 | Le et al. |
| 2018/0360540 A1 | 12/2018 | Le et al. |
| 2018/0365827 A1 | 12/2018 | Le et al. |
| 2019/0122361 A1 | 4/2019 | Le et al. |

FOREIGN PATENT DOCUMENTS

| | | |
|---|---|---|
| EP | 2389905 A1 | 11/2011 |
| EP | 3181050 A1 | 6/2017 |
| EP | 3389495 A1 | 10/2018 |
| EP | 3416131 A1 | 12/2018 |
| EP | 3639239 A1 | 4/2020 |
| GB | 2560666 A | 9/2018 |
| JP | 2014425 A | 1/2014 |
| TW | 201907413 A | 2/2019 |
| WO | 2002/087444 A1 | 11/2002 |
| WO | WO-2010/099359 A1 | 9/2010 |
| WO | WO-2010/120990 A1 | 10/2010 |
| WO | WO-2012/123029 A1 | 9/2012 |
| WO | 2015/117663 A1 | 8/2015 |
| WO | WO-2015/131234 A1 | 9/2015 |
| WO | WO-2016/118521 A1 | 7/2016 |
| WO | 2017103146 A1 | 6/2017 |
| WO | WO-2017/106794 A1 | 6/2017 |
| WO | WO-2017/177182 A1 | 10/2017 |
| WO | WO-2018/113984 A1 | 6/2018 |
| WO | 2018/229275 A1 | 12/2018 |
| WO | WO-2019/161477 A1 | 8/2019 |
| WO | WO-2020/231656 A2 | 11/2020 |

OTHER PUBLICATIONS

Written Opinion from international application No. PCT/EP2021/064697 dated Sep. 14, 2021.

International search report from international application No. PCT/EP2021/064697 dated Sep. 14, 2021.

* cited by examiner

CUSTOMIZATION OF INDIVIDUALIZED IMPLANT

TECHNICAL FIELD

The present disclosure relates generally to systems and methods for customizing an individualized implant suitable for repairing damage in an anatomical joint of a patient.

BACKGROUND

It is important to be able to determine damage to an anatomical joint, so that a suitable treatment may be proposed. Medical imaging of anatomical joints may be used as an aid in determining damage. Different medical imaging techniques are e.g. X-ray radiography, ultrasound, computed tomography (CT), nuclear medicine, positron emission tomography (PET) and magnetic resonance imaging (MRI).

The medical imaging generally takes place in a medical care facility, e.g. at a radiology department of a hospital. The images and the information obtained may be forwarded to an implant design center for design of an implant and resulting control software (CAD/CAM), e.g. to improve or repair damaged cartilage and/or bone, e.g. in a damaged joint such as a human knee or ankle.

PROBLEMS WITH THE PRIOR ART

In conventional prior art systems, implants may be manufactured as surgical kits in standard sizes and might be supplied with standard guides to support in implant surgery, e.g. to support in ensuring a correct position and mounting angle of the implant.

A problem with conventional systems is that implants are poorly customized to patients, and this may lead to replacement of unnecessary large areas of undamaged cartilage, and/or bad alignment of the top surface of the implant to the cartilage surface being replaced, which in turn may reduce the improvement in the condition of the person being subjected to implant surgery.

Therefore, there is a need for a system and method to improve the customizing an individualized implant suitable for repairing damage in an anatomical joint of a patient.

SUMMARY

The above described problems are addressed by the claimed system for customizing an individualized implant suitable for repairing damage in an anatomical joint of a patient. The system may comprise at least one processor configured to: i) obtain one or more medical image stacks of at least a part of the anatomical joint, wherein each of the medical image stacks are generated using a medical imaging system; ii) obtain a three-dimensional image representation of the at least part of the anatomical joint which is based on at least one of said medical image stacks; iii) determine damage to at least one of a plurality of anatomical structures in the anatomical joint by analyzing at least one of said one or more medical image stacks; iv) select an implant template to be used as a basis for a customized implant for repairing said determined damage from a predefined set of implant templates having predetermined types and sizes; v) generate a 3D model for visualization based on the three-dimensional image representation, in which 3D model the marked damage is visualized together with the selected implant template in a proposed position; vi) display the 3D model with functionality to enable manipulation of the 3D model; vii) receive an approval for said selected implant template in said proposed position; and viii) determine the final shape and dimensions of a customized implant suitable for repairing said determined damage based on said selected implant template and said proposed position.

In embodiments, the system comprises a storage media, and the medical image stacks are obtained from said storage media, wherein the medical image stacks have been uploaded into said storage media by personnel at a medical care facility, preferably the medical care facility where the generation of the medical image stacks using a medical imaging system has taken place. The uploading of the medical image stacks may however also be an automatic uploading directly from one system to another.

In embodiments, different users with different authorizations may interact with the system. Some users may be authorized only to upload images, some users may be authorized only to determine damage and/or propose an implant template and position, and some users may be authorized only to view the 3D model. Preferably, only one or more selected users, such as e.g. the physician, e.g. the surgeon, responsible for the patient, may submit an approval for the selected implant template in the proposed position. Thus, in embodiments, the system is configured to only accept an approval from a user with a specific approval authorization, such as e.g. the physician, e.g. the surgeon, responsible for the patient.

The above described problems are also addressed by the claimed method for customizing an individualized implant suitable for repairing damage in an anatomical joint of a patient. The method may comprise the steps of i) obtaining one or more medical image stacks of at least a part of the anatomical joint, wherein each of the medical image stacks are generated using a medical imaging system; ii) obtaining a three-dimensional image representation of the at least part of the anatomical joint which is based on at least one of said medical image stacks; iii) determining damage to at least one of a plurality of anatomical structures in the anatomical joint by analyzing at least one of said one or more medical image stacks; iv) selecting an implant template to be used as a basis for a customized implant for repairing said determined damage from a predefined set of implant templates having predetermined types and sizes; v) generating a 3D model for visualization based on the three-dimensional image representation, in which 3D model the marked damage is visualized together with the selected implant template in a proposed position; vi) displaying the 3D model with functionality to enable manipulation of the 3D model; vii) receiving an approval for said selected implant template in said proposed position; and viii) determining the final shape and dimensions of a customized implant suitable for repairing said determined damage based on said selected implant template and said proposed position.

In embodiments, the method comprises uploading the medical image stacks into a storage media by personnel at a medical care facility, preferably the medical care facility where the generation of the medical image stacks using a medical imaging system has taken place, wherein the obtaining of the medical image stacks comprises obtaining the medical image stacks from said storage media. The uploading of the medical image stacks may however also be an automatic uploading directly from one system to another.

There may be different users with different authorizations. Some users may be authorized only to upload images, some users may be authorized only to determine damage and/or propose an implant template and position, and some users may be authorized only to view the 3D model. Preferably, only one or more selected users, such as e.g. the physician, e.g. the surgeon, responsible for the patient, may submit an approval for the selected implant template in the proposed position. In embodiments, another person authorized by the physician may enter the approval into the system, after first receiving the approval from the physician. Thus, in embodiments, the approval is received from a user with a specific approval authorization, such as e.g. the physician responsible for the patient.

In embodiments, the plurality of anatomical structures are anatomical structures of the knee joint selected from the group comprising the femur, patella, tibia, fibula, cartilage, menisci, cruciate ligaments and tendons. The plurality of anatomical structures may alternatively comprise a different selection of different parts of bone, cartilage, ligaments and/or tendons, especially if the anatomical joint is not a knee, such as e.g. if the anatomical joint is an ankle.

The implant template should be selected to have a type and dimensions that match a determined damage, thereby making it suitable for repairing the determined damage.

In embodiments, the proposed position of the selected implant template is a position where the selected implant template covers at least a major part of the determined damage, and a position that also minimizes at least one of the total volume of tissue, such as bone and/or cartilage, to be removed for implanting the customized implant, and/or the surface area of the implant penetration into the bone. Severe lesions should preferably have a surface coverage of at least 90%.

In embodiments, the determining of the final shape and dimensions of the customized implant suitable for repairing said determined damage comprises simulating a healthy surface at said proposed position, and designing the surface of the customized implant to match said simulated healthy surface. A healthy surface is a surface that is whole and not subject to the damage which is typically a void, tear, or lesion in the material of the surface. The healthy surface may e.g. be simulated based on the curvature of the cartilage surrounding the area of damaged cartilage, especially when the anatomical joint is a knee joint. However, the healthy surface may also be simulated based on the curvature of the bone surface surrounding the area of bone damage, especially when the determined damage is damage to the talus, where the damage to be repaired is generally bone damage.

In embodiments, the predefined set of implant templates comprises implants having implant hats ("hat" here meaning a pattern which interfaces with the anatomical area that is concerned by covering at least a portion of the area and specifically covering the area that is subject to the damage of concern) that have a substantially circular shape in outline and implants having implant hats that are shaped to comprise at least two overlapping substantially circular shapes in outline. Circular outline shapes make the creation of the implant recess during surgery easier, since the recess can be created by simply drilling. The implants also include means in the form of one or more anchors/pegs/posts to secure the implant at the site by penetrating the underlying bone, where the positions and angles of the one or more anchors/pegs/posts can be varied to optimize the effect of the implant. The implant templates in the predefined set of implant templates thus have different positions and angles for the one or more anchors/pegs/posts.

In embodiments, the functionality to enable manipulation of the 3D model comprises functionality to select at least one medical image in the medical image stack to visualize through interaction with the 3D model, and functionality to, in the 3D model, visualize the position of at least one medical image that is currently visualized.

In embodiments, the final shape and dimensions of the customized implant (including specifically the outline of the implant, the topography of the top surface and the configuration of the implant anchor/peg/post) are output as parameters for manufacturing the customized implant.

The above described problems are also addressed by a non-transitory machine-readable medium on which is stored machine-readable code which, when executed by a processor, controls the processor to perform any one of the above described methods.

The medical imaging system may e.g. be a magnetic resonance imaging (MRI) system, an x-ray imaging system, an ultrasonic imaging system, a fluoroscopic imaging system and/or a computer tomography (CT) system. A medical image stack is a number of images in a series captured during a process of scanning through different layers of the anatomical joint or part of it using a medical imaging system.

The processor may in some embodiments comprise several different processors which together perform the claimed functions.

The term "physician" in this application covers any licensed and authorized care provider who is responsible for the treatment of the patient.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Introduction

The present disclosure relates generally to systems and methods for customizing an individualized implant suitable for repairing damage in an anatomical joint of a patient, including humans and other animals.

In some embodiments, the anatomical joint is a knee. In other embodiments, the anatomical joint may be any other anatomical joint suitable for damage determination using image data analysis, such as an ankle, a hip, a toe, an elbow, a shoulder, a finger or a wrist. Further, often only a part of the joint is of interest, such as e.g. the femoral part of the knee joint, or the proximal talar surface of the ankle.

In one or more embodiments, the plurality of anatomical structures are anatomical structures of the knee joint selected from the group comprising the femur, patella, tibia, fibula, cartilage, menisci, cruciate ligaments and tendons. The plurality of anatomical structures may alternatively comprise a different selection of different parts of bone, cartilage, ligaments and/or tendons, especially if the anatomical joint is not a knee, such as e.g. if the anatomical joint is an ankle. The anatomical structures are preferably structures that are relevant to a user who uses the graphical user interface to evaluate the condition of an anatomical joint.

In a non-limiting example, the anatomical joint is a knee and the damage that is determined is related to the femoral part of the knee joint, such as chondral and/or osteochondral lesions. In another non-limiting example, the anatomical joint is an ankle and the damage that is determined is related to the talus.

A 3D model is an advantageous way of visualizing damage to bone, cartilage and other tissues. In order for medical personnel to review a proposed treatment such as a proposed implant to be used for damage repair, it is advantageous to visualize such a proposed implant together with the damage in a 3D model.

System and method embodiments of the disclosed solution are presented in more detail in connection with the figures.

System Architecture

Figure 1:
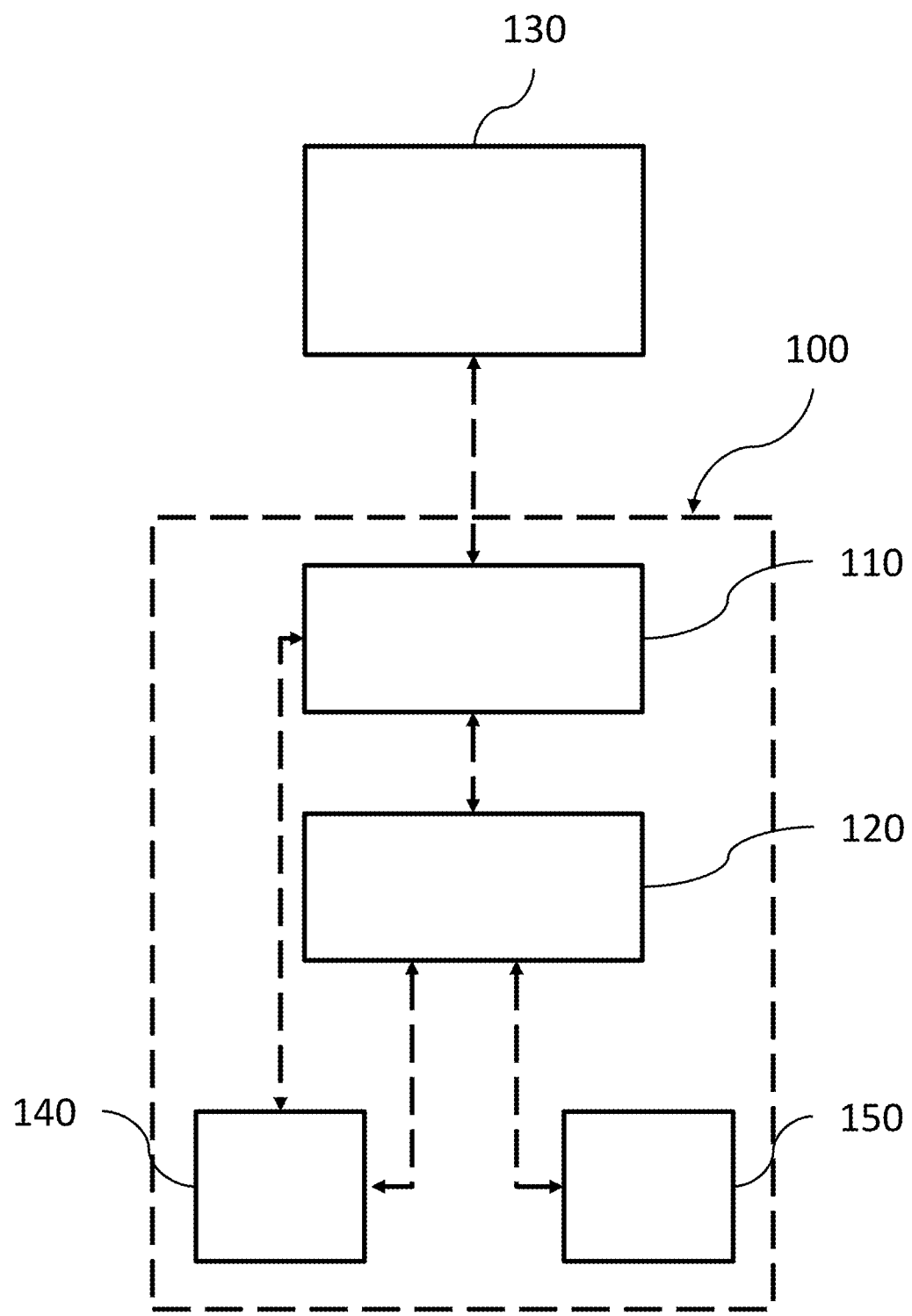
FIG. 1 shows a schematic view of a system for customizing an individualized implant suitable for repairing damage in an anatomical joint of a patient, in accordance with one or more embodiments described herein.

FIG. 1 shows a schematic view of a system 100 for customizing an individualized implant suitable for repairing damage in an anatomical joint of a patient. According to embodiments, the system 100 comprises a display 140, at least one manipulation tool 150, and a storage media 110, configured to receive and store image data and parameters. In some embodiments, the system 100 is communicatively coupled to a medical imaging system 130. The medical imaging system 130 may be configured to capture or generate medical images, e.g. radiology images such as X-ray images, ultrasound images, computed tomography (CT) images, nuclear medicine including positron emission tomography (PET) images, and magnetic resonance imaging (MRI) images. The storage media 110 may be configured to receive and store medical image stacks from the medical imaging system 130. In embodiments, medical image stacks are uploaded into the storage media 110 by personnel at a medical care facility, preferably the medical care facility where the medical imaging takes place. Medical image stacks may however also be uploaded into the storage media 110 by another medical care facility, or by other authorized personnel. The uploading of the medical image stacks may also be an automatic uploading directly from one system to another.

In one or more embodiments, the system 100 comprises at least one processor 120 configured to: i) obtain one or more medical image stacks of at least a part of the anatomical joint, wherein each of the medical image stacks are generated using a medical imaging system 130; ii) obtain a three-dimensional image representation of the at least part of the anatomical joint which is based on at least one of said medical image stacks; iii) determine damage to at least one of a plurality of anatomical structures in the anatomical joint by analyzing at least one of said one or more medical image stacks; iv) select an implant template to be used as a basis for a customized implant for repairing said determined damage from a predefined set of implant templates having predetermined types and sizes; v) generate a 3D model for visualization based on the three-dimensional image representation, in which 3D model the marked damage is visualized together with the selected implant template in a proposed position; vi) display the 3D model with functionality to enable manipulation of the 3D model; vii) receive an approval for said selected implant template in said proposed position; and viii) determine the final shape and dimensions of a customized implant suitable for repairing said determined damage based on said selected implant template and said proposed position. The medical imaging system may e.g. be a magnetic resonance imaging (MRI) system, an x-ray imaging system, an ultrasonic imaging system, a fluoroscopic imaging system and/or a computer tomography (CT) system.

In embodiments, the system comprises a storage media 110, and the medical image stacks are obtained from said storage media 110, wherein the medical image stacks have been uploaded into said storage media 110 by personnel at a medical care facility, preferably the medical care facility where the generation of the medical image stacks using a medical imaging system 130 has taken place. Medical image stacks may however also be uploaded into the storage media 110 by personnel at another medical care facility, or by other authorized personnel. The uploading of the medical image stacks may also be an automatic uploading directly from one system to another.

In embodiments, different users with different authorizations may interact with the system 100. Some users may be authorized only to upload images, some users may be authorized only to determine damage and/or propose an implant template and position, and some users may be authorized only to view the 3D model. Preferably, only one or more selected users, such as e.g. the physician, e.g. the surgeon, responsible for the patient, may submit an approval for the selected implant template in the proposed position. Thus, in embodiments, the approval is received from a user with a specific approval authorization, such as e.g. the physician responsible for the patient.

Thus, the at least one processor 120 may be configured to determine damage to an anatomical joint, select an implant template to be used as a basis for a customized implant for repairing the determined damage, and visualize the selected implant template in a proposed position in a 3D model that also visualizes the determined damage. This visualization may be provided to a medical staff member such as e.g. a physician, e.g. a surgeon, who may approve or reject the proposed implant template in the proposed position. If the physician approves, the at least one processor 120 may be configured to determine the final shape and dimensions of a customized implant suitable for repairing said determined damage based on said selected implant template and said proposed position. The final shape and dimensions may then be output as parameters for manufacturing the customized implant, e.g. by being sent to an implant manufacturer.

In embodiments, the proposed position of the selected implant template is a position where the selected implant template covers at least a major part of the determined damage, and a position that also minimizes at least one of the total volume of tissue, such as bone and/or cartilage, to be removed for implanting the customized implant, and/or the surface area of the implant penetration into the bone.

The determined damage may be marked as more or less severe. Damage that is very mild may not need repairing, but lesions should preferably have a surface coverage of at least 90%

In embodiments, the predefined set of implant templates comprises implants having implant hats that have a substantially circular shape in outline and implants having implant hats that are shaped to comprise at least two overlapping substantially circular shapes in outline.

The implant template is thus preferably selected from a predefined set of implant templates having predetermined types and sizes, e.g. varying outline dimensions, as well as varying positions and angles of the means to secure the implant in place. In this context, a suitable implant means an implant having a type and dimensions that match a determined damage, thereby making it suitable for repairing the determined damage. In one or more embodiments, the processor may be configured to visualize the selected implant in the 3D model.

The determination of the final shape and dimensions of a customized implant suitable for repairing the determined damage based on the selected implant template and the proposed position preferably involves designing an implant surface that corresponds to a 3D image of a simulated healthy cartilage surface.

It is desirable to simulate a healthy cartilage surface as closely as possible. If just the 3D curvature of the subchondral bone subjacent to the area of damaged cartilage is used for designing the surface of the implant, this does not necessarily correspond to a simulated healthy cartilage surface, since the cartilage does not necessarily have uniform thickness, especially when the anatomical joint is a knee joint. However, the healthy surface may be simulated based on the curvature of the bone surface surrounding the area of bone damage in joints where the cartilage has uniform thickness, such as in the talus, where the damage to be repaired is generally bone damage.

According to embodiments, the implant surface is instead simulated based on the curvature of the cartilage surrounding the area of damaged cartilage. Preferably, a suitable area comprising and extending around the damaged cartilage is selected, and the curvature of the whole area is simulated in such a way that the curvature of the area which is not damaged matches the actual curvature, and a simulated healthy surface of the area of damaged cartilage is generated. The simulation may comprise an interpolation, e.g. using the Solid Works Surface Wizard or another suitable tool.

FIGS. 2a-d and 3a-d show the design of the surface of an implant having a surface which corresponds to a 3D image of a simulated healthy cartilage surface. FIGS. 2a-d show the design of the surface of an implant with a circular surface area and FIGS. 3a-d show the design of the surface of an implant with a surface area corresponding to two overlapping circles.

Figure 2A:
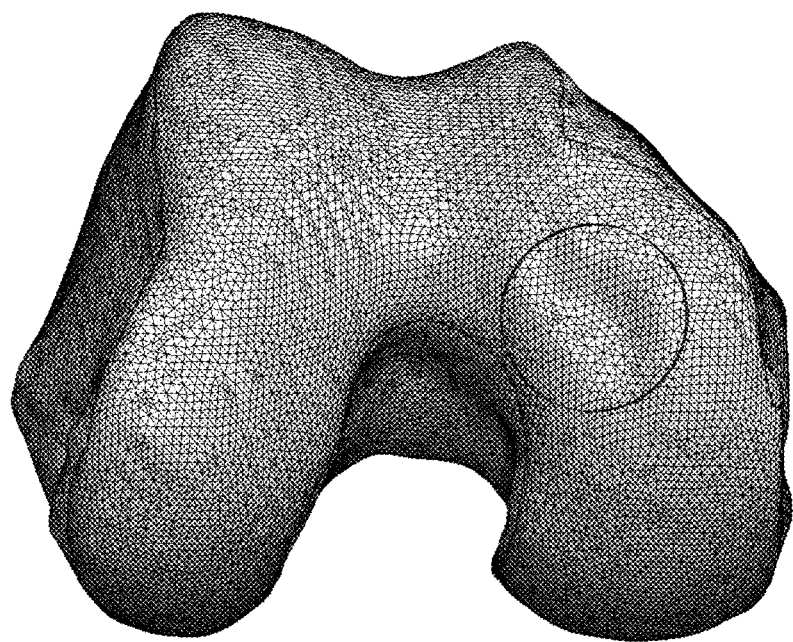
FIGS. 2a-d show the design of the surface of an implant having a circular surface area that corresponds to a 3D image of a simulated healthy cartilage surface, in accordance with one or more embodiments described herein.
Figure 3A:
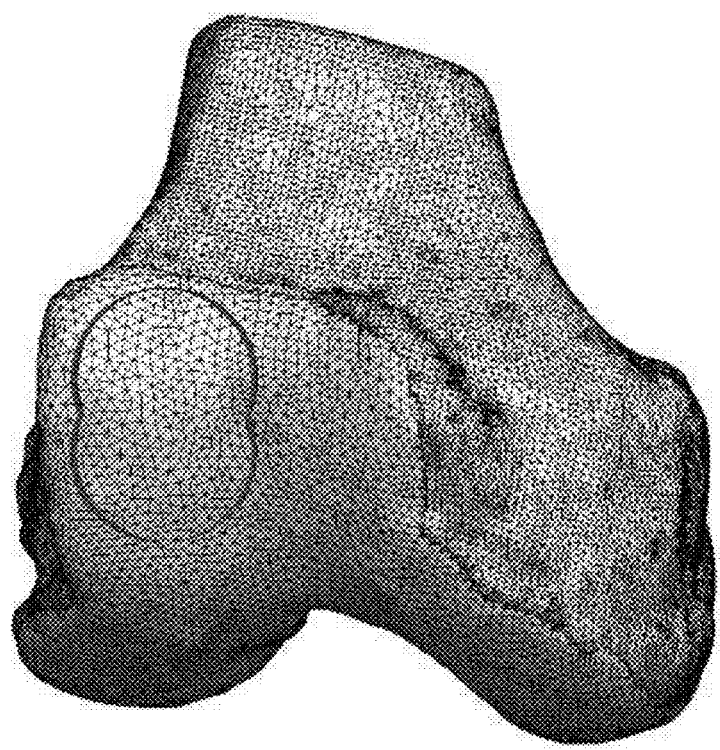
FIGS. 3a-d show the design of the surface of an implant having a surface area of two overlapping circles that corresponds to a 3D image of a simulated healthy cartilage surface, in accordance with one or more embodiments described herein.

FIGS. 2a and 3a show an image of a 3D mesh model of the cartilage and bone of a knee. The mesh model may be created based on any suitable imaging methods, such as e.g. MRI. In the image of the mesh model, the implant position has been marked with a circle in FIG. 2a, and two overlapping circles, a combined or "twin" circle, in FIG. 3a. The circle, or "twin" circle, corresponds to the circumferential outline shape of the implant hat of the proposed implant. At least parts of the surface within this circle or "twin" circle comprises damaged cartilage, and possibly also damaged subchondral bone beneath the cartilage. The size of the implant hat is selected based on the extent of damage, so that at least most of the damaged area is removed and replaced by the implant. Sometimes all of the surface within the circle will be damaged, and some of the damaged area will not be removed, and sometimes the volume to be removed will comprise also some healthy cartilage and/or subchondral bone.

Figure 2B:
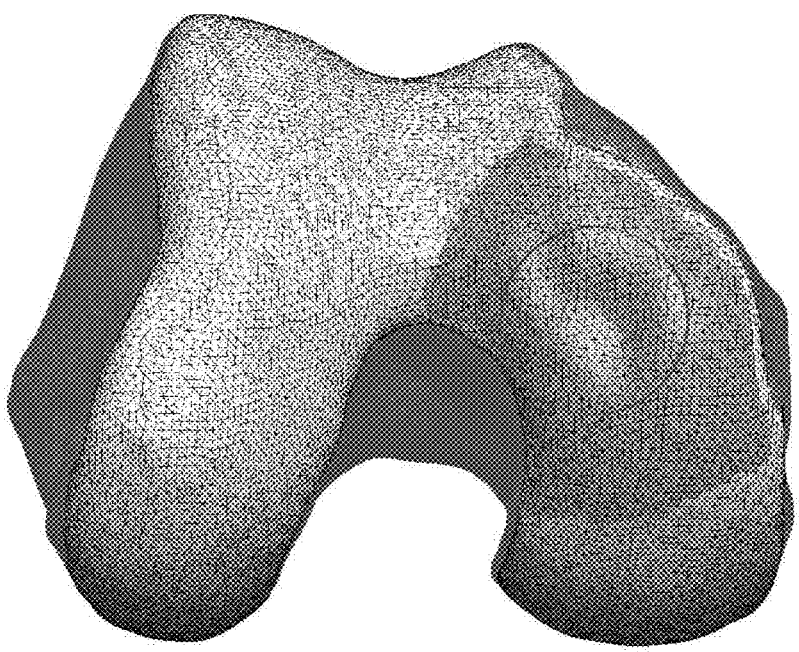
Figure 3B:
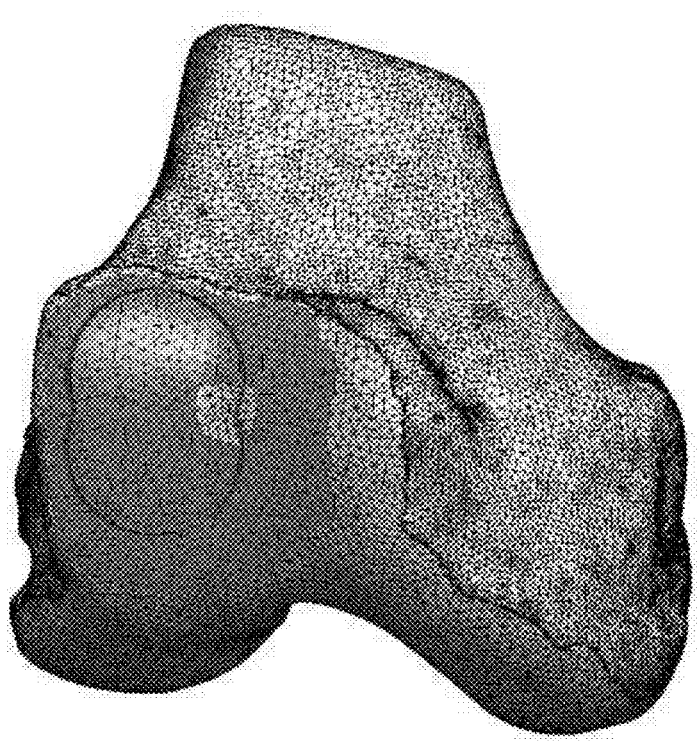

FIGS. 2b and 3b show the selection of a suitable area for simulating the curvature of the surface. The area is preferably large enough to have sufficient curvature in all directions surrounding the area of damaged cartilage, without containing any sharp edges which could distort the simulation. The area may e.g. be selected based on the distance from the damaged cartilage and the curvature, e.g. so that the whole area within a predetermined distance from the damaged cartilage is selected provided that the curvature within this area is below a certain threshold. Sections falling within a predetermined distance from the damaged cartilage but exceeding the curvature threshold would then be excluded from the area.

Figure 2C:
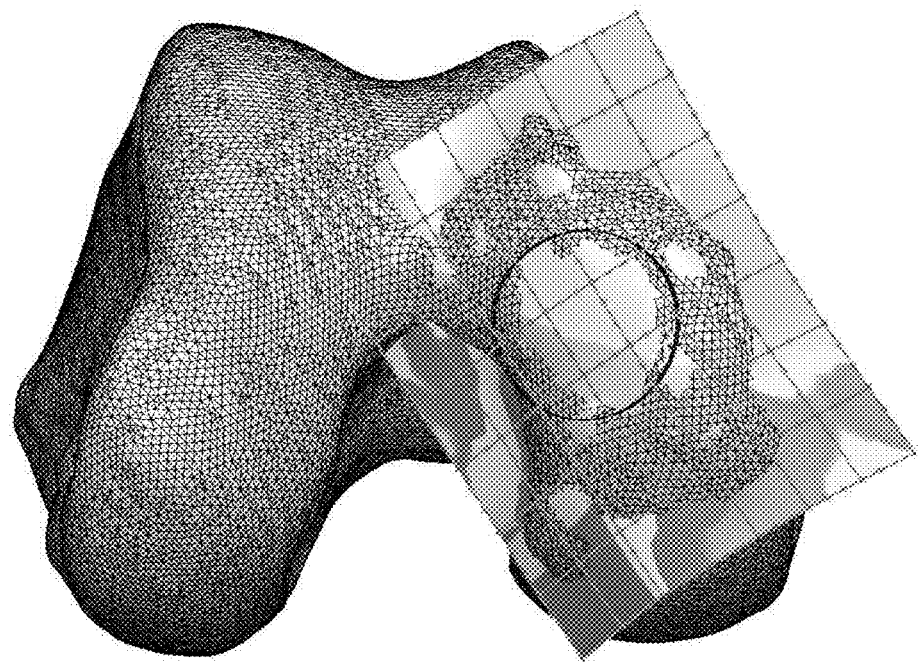
Figure 3C:
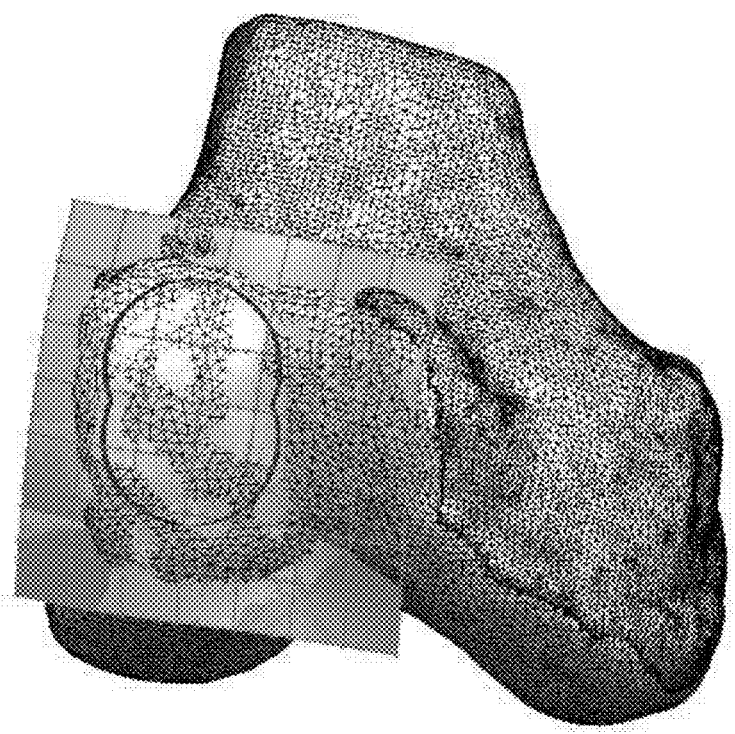

FIGS. 2c and 3c show a simulation of the curvature of the whole area, including a tangent interpolation over the area of damaged cartilage. The generated surface is defined by curvature lines along the length and the width, points along which curvature lines coincide with the points of the 3D mesh model in the areas of healthy cartilage. Only healthy cartilage surfaces are used as a basis for this tangent interpolation; all potentially damaged areas are excluded. In FIGS. 2c and 3c, the healthy mesh areas shown with triangles within the surface generating grid are used as a basis for the tangent interpolation, and the blank areas are excluded. Preferably, all areas of damaged cartilage are excluded from being the basis of the interpolation. After the interpolation, the deviation between the interpolated area and the actual area within the areas of healthy cartilage may be analyzed in order to ascertain that the interpolated area does not differ too much from the actual area in the areas of healthy cartilage. If there is too much deviation, a new interpolation may be necessary.

Figure 2D:
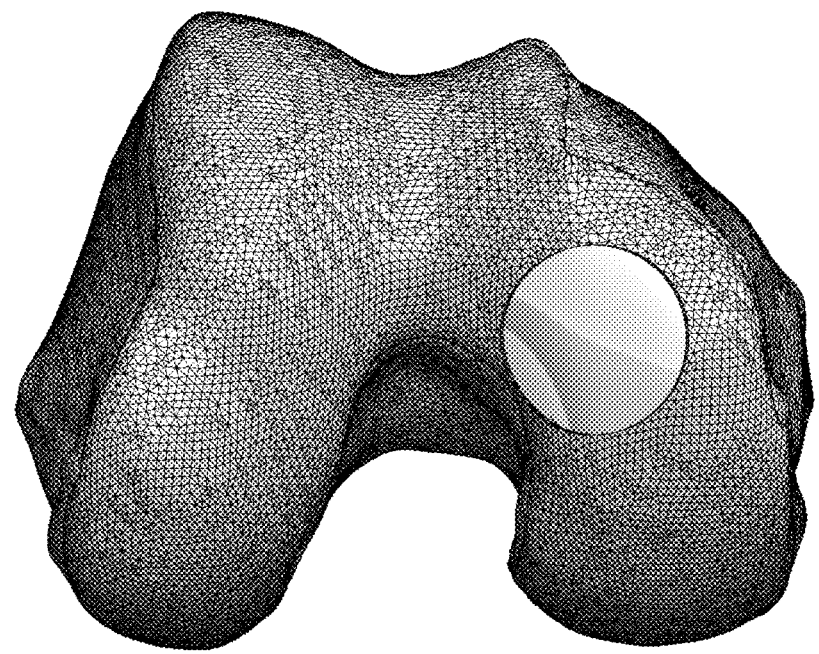
Figure 3D:
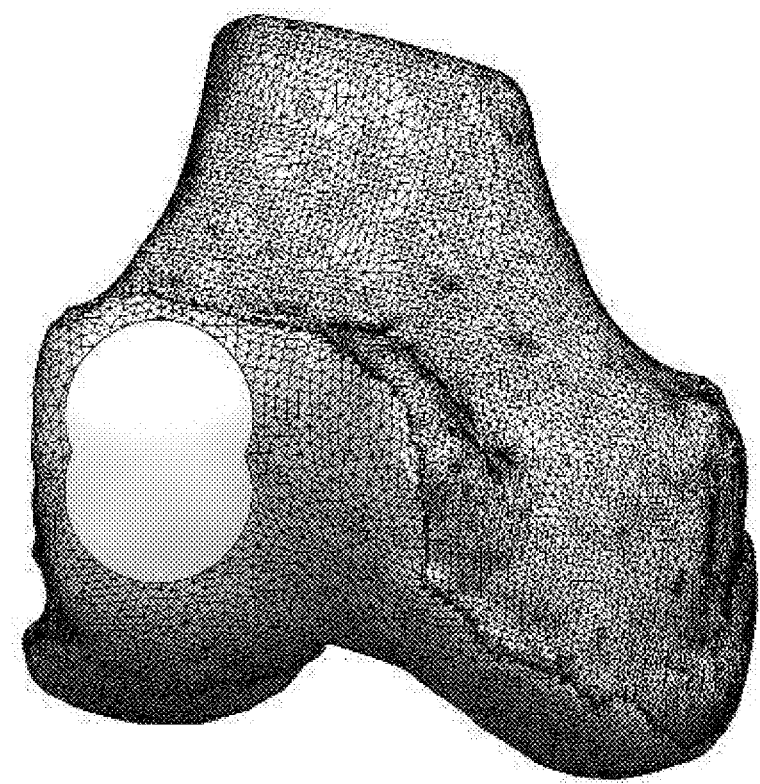

When the healthy cartilage surface has been simulated, the area is trimmed to match the implant size, as shown in FIGS. 2d and 3d. A 3D mesh model of the cartilage and bone of the knee comprising the implant is then generated, so that it can be determined that the knee with the implant matches the surrounding surfaces. This evaluation may e.g. be done layer by layer in the MRI software.

Figure 4A:
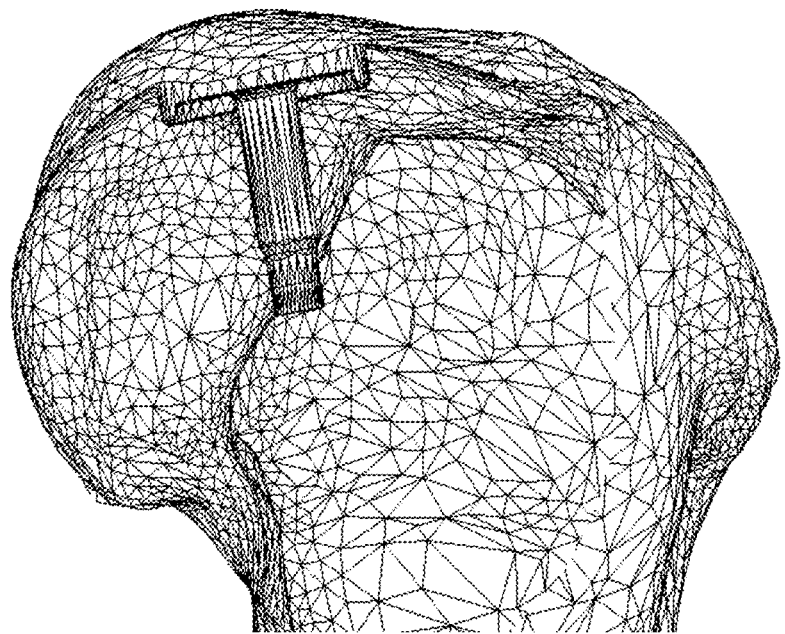
FIGS. 4a-b show an implant with an implant hat and an implant post/peg, positioned at different depths and axis tilts in a joint, in accordance with one or more embodiments described herein.
Figure 4B:
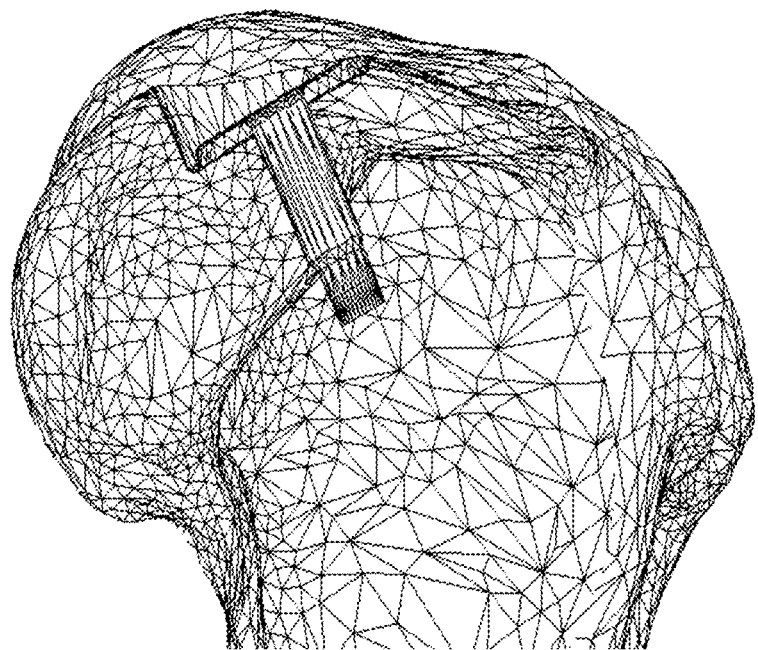

The depth and the axis tilt of the implant may be optimized in order to minimize the total penetration of the implant into the bone. FIGS. 4a-b show an implant with an implant hat and an implant post/peg, positioned at different depths and axis tilts in a joint. The optimization may be done by positioning the implant and tilting the implant axis so that the implant hat will at all points be thick enough to ensure mechanical stability, and preferably also thick enough to ensure firm anchoring towards cartilage and bone. This may mean that the implant hat at each point of its circumference must penetrate at least a predetermined minimum depth into the bone. This ensures that the whole of the implant hat will have at least a minimum thickness, and will thus not easily break.

The optimization of the tilt of the implant axis may involve minimizing the maximum penetration depth into the bone along the circumference of the implant hat. This ensures that the hole to be drilled in the bone will not become deeper than necessary. The optimization of the tilt of the implant axis may alternatively involve minimizing the total volume of tissue, such as bone and/or cartilage, to be removed for implanting the implant. This optimization is especially advantageous when implanting a combined, "twin", implant having more than one implant axis. The optimization of the tilt of the implant axis may alternatively involve minimizing the surface area of the implant penetration into the bone. The surface area may e.g. be determined by multiplying the average depth of the hole to be drilled in the bone by the circumference.

When the position and axis tilt of the implant has been determined in this way, an implant may be designed to have a final shape and dimensions according to the determined position and axis tilt, with a surface corresponding to the simulated healthy cartilage surface described above in relation to FIGS. 2a-d and 3a-d.

In embodiments, the at least one processor 120 is configured to also output the final shape and dimensions of said customized implant as parameters for manufacturing said customized implant.

The at least one processor 120 may for example be a general data processor, or other circuit or integrated circuit capable of executing instructions to perform various processing operations. The at least one processor 120 may in some embodiments comprise several different processors 120 which together perform the claimed functions. In the same way, the storage media 110 may in some embodiments comprise several different storage media 110 which together perform the claimed functions.

In embodiments, the medical image stacks are uploaded into the storage media 110 by personnel at a medical care facility, preferably the medical care facility where the medical imaging takes place. Medical image stacks may however also be uploaded into the storage media 110 by personnel at another medical care facility, or by other authorized personnel. The uploading of the medical image stacks may also be an automatic uploading directly from one system to another.

The display 140 may be configured to receive image data for display via the processor 120, and/or to retrieve image data for display directly from the storage media 110, possibly in response to a control signal received from the processor 120 or the at least one manipulation tool 150.

In one or more embodiments, the at least one processor 120 is configured to determine damage to at least one of a plurality of anatomical structures in the anatomical joint. The at least one processor 120 may e.g. determine damage by detecting that the intensity in an area within or adjacent to the bone and/or cartilage parts of the anatomical joint is higher or lower than a predetermined threshold. Depending on the settings of the imaging device that has captured the analyzed medical image data, the analyzed image may for example represent the following substances with different intensity levels: cortical bone, fluid/liquids, cartilage, tendons, ligaments, fat/bone marrow and menisci. It is for example an indication of damage if fluid is detected where there in a healthy joint should be no fluid. If fluid is detected next to abnormalities in the cartilage, this can also be an indication of damage. Different intensity levels in the analyzed image correspond to different signal intensity levels, and these may typically be represented by pixel/voxel values ranging from 0 to 1, or in a visual representation shown as grey scale levels from white to black. In embodiments where the pixel/voxel values range from 0 to 1, a predetermined threshold is set to a suitable value between 0 and 1, or in other words to a suitable grey scale value. The at least one processor 120 may be configured to use an algorithm determined by a machine learning system in the damage determination. Such a machine learning system may e.g. be trained using images where manually determined damage has been marked.

In one or more embodiments, the at least one processor 120 may further, or alternatively, be configured to detect an irregular shape of at least one tissue part of the anatomical joint and determine whether this represents a damage to the anatomical joint. In one or more embodiments the at least one processor 120 may further, or alternatively, be configured to make a comparison of an identified tissue part in a damage image with a template representing a predefined damage pattern for an anatomical joint. In some embodiments, such a determination may include comparing a detected irregular shape of the contour with a template representing a predefined damage pattern for an anatomical joint, and/or comparing a detected intensity for a certain area with a template representing a predefined damage pattern for an anatomical joint. The at least one processor 120 may be configured to use an algorithm determined by a machine learning system also for these steps.

The at least one processor 120 may thus use a machine learning system in determining damage to the at least one of the plurality of anatomical structures in the anatomical joint. Such a machine learning system may e.g. be trained using images where damage has been manually marked, and may thereby learn to correlate different types of features and/or deviations in the images with damage.

In one or more embodiments, the processor 120 may be configured to mark the determined damage to the anatomical joint in the medical images. To mark the determined damage, the processor 120 may be configured to change the pixel/voxel value of one or more pixels/voxels on, in connection with, or surrounding a pixel/voxel identified to belong to a determined damage, such that the determined damage is visually distinguished and noticeable to a user/viewer, by performing a selection of the following: changing the luminance/intensity values of one or more pixels/voxels identified as being located on a determined damage; changing one or more chrominance/color values of one or more pixels/voxels identified as being located on a determined damage; changing the luminance/intensity values of one or more pixels/voxels identified as surrounding a determined damage; changing one or more chrominance/color values of one or more pixels/voxels identified as surrounding a determined damage; and/or adding an annotation, symbol or other damage indicator to the image, in connection with one or more pixels/voxels identified as being located on, or surrounding, a determined damage.

In one or more embodiments, the processor 120 may be configured to mark the determined damage to the anatomical joint in the obtained three-dimensional image representation of the anatomical joint or part of it. To mark the determined damage, the processor 120 may be configured to change the voxel value of one or more voxels on, in connection with, or surrounding a voxel identified to belong to a determined damage, such that the determined damage is visually distinguished and noticeable to a user/viewer, by performing a selection of the following: changing the luminance/intensity values of one or more voxels identified as being located on a determined damage; changing one or more chrominance/color values of one or more voxels identified as being located on a determined damage; changing the luminance/intensity values of one or more voxels identified as surrounding a determined damage; changing one or more chrominance/color values of one or more voxels identified as surrounding a determined damage; and/or adding an annotation, symbol or other damage indicator to the image, in connection with one or more voxels identified as being located on, or surrounding, a determined damage.

The at least one manipulation tool 150 is typically configured to interpret received user input and to generate control signals in response to said received user input. The display 140 and the at least one manipulation tool 150 may be integrated in, connected to or communicatively coupled to the system 100. The at least one manipulation tool 150 may for instance be configured to interpret received user input that is being input in connection with the 3D model, and generate control signals in response to said received user input, to trigger display of an image or manipulation of image data being displayed, wherein the manipulation may be temporary or permanent. Such manipulations may for example include providing annotations, moving or changing an image or part of an image, changing the viewing perspective, zooming in or out, and/or any other suitable form of manipulation that enables the user to view and analyze the displayed image data in an improved manner. The at least one manipulation tool 150 may for example comprise a selection of a keyboard, a computer mouse, one or more buttons, touch functionality, a joystick, and/or any other suitable input device. In some embodiments, the processor 120 may be configured to receive a control signal from the at least one manipulation tool 150 and to process image data that is being displayed, or in other words manipulate a displayed image, in response to the received control signal.

The processor 120 may be configured to use a different medical image stack for obtaining the three-dimensional image representation than each of the medical image stacks used for determining damage to the identified tissue parts in the anatomical joint. In this way, the unique set of parameters used for generating each medical image stack can be optimized to the use of the medical image stack.

A 3D model may be advantageous for visualizing damage to bone, cartilage and other tissues. The DICOM format, or a comparable medical image file format, may be advantageous for visualizing different parts of the anatomical joint. It may therefore be useful if there is functionality to enable manipulation of the 3D model that comprises functionality to select at least one medical image in the medical image stack to visualize through interaction with the 3D model. In embodiments, the functionality to enable manipulation of the 3D model therefore comprises functionality to select at least one medical image in the medical image stack to visualize through interaction with the 3D model, and functionality to, in the 3D model, visualize the position of at least one medical image that is currently visualized.

The 3D model may be used for visualizing anatomical structures such as different parts of bone, ligaments, tendons and/or cartilage, e.g. anatomical structures of the knee joint selected from the group comprising the femur, patella, tibia, fibula, cartilage, menisci, cruciate ligaments and tendons, and damage in relation to the anatomical joint that is being investigated.

In the generated 3D model, a position indication of an implant template suitable for repairing the determined damage is preferably visualized. In this context, a suitable implant template means an implant template having a type and dimensions that match a determined damage, thereby making it suitable for repairing the determined damage. Such a suitable implant template is preferably visualized in the 3D model and/or the displayed medical image.

In some embodiments, the generated 3D model further indicates anatomical deviations which do not in themselves constitute damage to the joint. Such anatomical deviations may e.g. affect the choice of treatment for the determined damage. As a non-limiting example, severe osteophyte problems may indicate other problems, where an implant may not improve the situation.

The generated 3D model may for example be obtained based on a medical image stack captured during a process of scanning images through different layers of the anatomical joint or part of it. A medical image stack is thus a number of images in a series captured during a process of scanning through different layers of the anatomical joint or part of it.

Each medical image stack may e.g. be generated during a scanning process using a specific sequence, comprising a unique set of parameters that differs from the set of parameters used for generating the other medical image stacks. Such a scanning process may be any type of scanning process for generating medical image stacks, where different sets of parameters may be used to generate medical image stacks with different types of detail. The use of different specific sequences for different uses of the medical image stacks allows the visualization of more detail in the images, since some types of detail may be more clearly visible using one set of parameters and other types of detail may be more clearly visible using another set of parameters. It may e.g. be useful to use an adapted sequence in the scanning process for generating the medical image stack used for generating the 3D model, since the requirements on such a medical image stack are different from the requirements on the medical image stack used for typical damage determination.

The scanning processes used for generating the medical image stacks may e.g. be MR scanning processes using different specific MR sequences, where each specific MR sequence uses a unique set of MR parameters. The MR parameters may e.g. be the repetition time TR (the time between the RF pulses) and the echo time TE (the time between an RF pulse and its echo). Depending on the desired information, the set of MR parameters may e.g. cause a T1 weighted MR sequence if a short TR and a short TE is selected, a T2 weighted MR sequence if a long TR and a long TE is selected, or an intermediately weighted MR sequence of a long TR and a short TE is selected. The different sets of MR parameters do not necessarily have to cause MR sequences of different types—two different sets of MR parameters may e.g. both cause T1 weighted sequences, but one of the sets may cause a stronger T1 weighting than the other. There are also other MR parameters, such as e.g.

flip angle, bandwidth or different types of fat suppression or enhancement of gadolinium, which may be varied between the MR sequences In MR scanning, it may be advantageous to use very different sets of MR parameters for generating the medical image stack used for generating the 3D model and for generating the other medical image stacks. It may e.g. be advantageous to use a specific 3D MRI sequence for generating the medical image stack used for generating the 3D model. In a 2D MRI sequence, each radiofrequency (RF) pulse excites a narrow slice, and magnetic field gradients are applied in two directions parallel to the plane in order to analyze the result. Such slices may then be combined into a 3D volume. In a 3D MRI sequence, on the other hand, each RF pulse excites the entire imaging volume, and magnetic field gradients are applied in three directions in order to analyze the result. In this way, a 3D volume may be created directly. Encoding (e.g. phase encoding) may be used to discriminate spatially.

The scanning processes used for generating the medical image stacks may also be CT scanning processes using different specific CT sequences, where each specific CT sequence uses a unique set of CT parameters. The CT parameters may e.g. be the tube potential (kV), the tube current (mA), the tube current product (mAs), the effective tube current-time product (mAs/slice), the tube current modulation (TCM), the table feed per rotation (pitch), the detector configuration, the collimation, the reconstruction algorithm, the patient positioning, the scan range and/or the reconstructed slice thickness. Also in CT scanning, it may be advantageous to use very different sets of CT parameters for generating the medical image stack used for generating the 3D model and for generating the other medical image stacks.

A 3D model may alternatively be constructed directly from a series a series of 2D images produced by a medical imaging device, such as e.g. a magnetic resonance imaging (MRI) system, an x-ray imaging system, an ultrasonic imaging system, a fluoroscopic imaging system and/or a computer tomography (CT) system.

The processor 120 may further be configured to perform any or all of the method steps of any or all of the embodiments presented herein.

Method Embodiments

Figure 5:
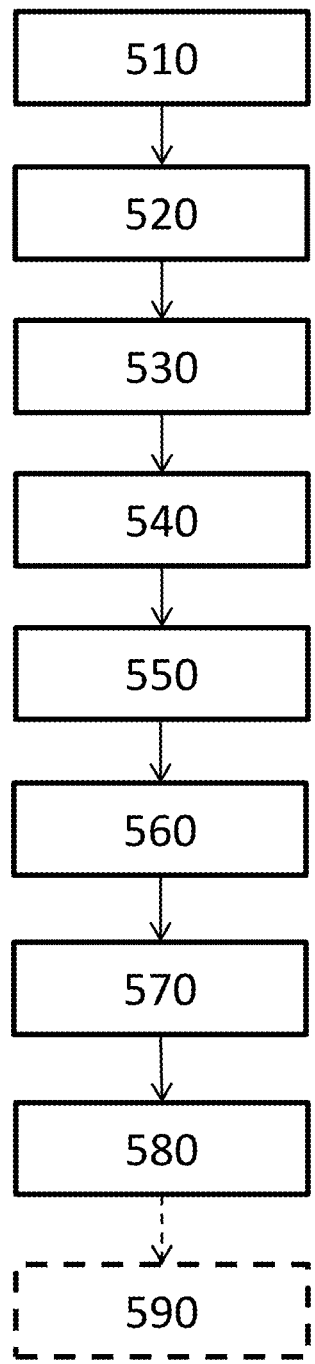
FIG. 5 is a schematic flow diagram for a method for customizing an individualized implant suitable for repairing damage in an anatomical joint of a patient, in accordance with one or more embodiments described herein.

FIG. 5 is a flow diagram of embodiments of a method for customizing an individualized implant suitable for repairing damage in an anatomical joint of a patient. In accordance with one or more to embodiments, the method 500 comprises:

In step 510: obtaining one or more medical image stacks of at least a part of the anatomical joint, wherein each of the medical image stacks are generated using a medical imaging system 130.

In step 520: obtaining a three-dimensional image representation of the at least part of the anatomical joint which is based on at least one of said medical image stacks.

In step 530: determining damage to at least one of a plurality of anatomical structures in the anatomical joint by analyzing at least one of said one or more medical image stacks.

In step 540: selecting an implant template to be used as a basis for a customized implant for repairing said determined damage from a predefined set of implant templates having predetermined types and sizes.

In step 550: generating a 3D model for visualization based on the three-dimensional image representation, in which 3D model the marked damage is visualized together with the selected implant template in a proposed position.

In step 560: displaying the 3D model with functionality to enable manipulation of the 3D model, e.g. on display 140.

In step 570: receiving an approval for said selected implant template in said proposed position.

In step 580: determining the final shape and dimensions of a customized implant suitable for repairing said determined damage based on said selected implant template and said proposed position.

The medical imaging system may e.g. be a magnetic resonance imaging (MRI) system, an x-ray imaging system, an ultrasonic imaging system, a fluoroscopic imaging system and/or a computer tomography (CT) system.

The method may further comprise at least one of the following:

In step 505: uploading the medical image stacks into a storage media 110 by personnel at a medical care facility, preferably the medical care facility where the generation of the medical image stacks using a medical imaging system 130 has taken place, wherein the obtaining 510 of the medical image stacks comprises obtaining 510 the medical image stacks from said storage media 110.

In step 590: outputting the final shape and dimensions of the customized implant as parameters for manufacturing said customized implant.

There may be different users with different authorizations. Some users may be authorized only to upload images, some users may be authorized only to determine damage and/or propose an implant template and position, and some users may be authorized only to view the 3D model. Preferably, only one or more selected users, such as e.g. the physician, e.g. the surgeon, responsible for the patient, may submit an approval for the selected implant template in the proposed position. Thus, in embodiments, the approval is received from a user with a specific approval authorization, such as e.g. the physician responsible for the patient.

In embodiments, the plurality of anatomical structures are anatomical structures of the knee joint selected from the group comprising the femur, patella, tibia, fibula, cartilage, menisci, cruciate ligaments and tendons. The plurality of anatomical structures may alternatively comprise a different selection of different parts of bone, cartilage, ligaments and/or tendons, especially if the anatomical joint is not a knee, such as e.g. if the anatomical joint is an ankle.

In some embodiments, the anatomical joint is a knee. In other embodiments, the anatomical joint may be any other anatomical joint suitable for damage determination using image data analysis, such as ankle, a hip, a toe, an elbow, a shoulder, a finger or a wrist.

In embodiments, the proposed position of the selected implant template is a position where the selected implant template covers at least a major part of the determined damage, and a position that also minimizes at least one of the total volume of tissue, such as bone and/or cartilage, to be removed for implanting the customized implant, and/or the surface area of the implant penetration into the bone.

The determined damage may be marked as more or less severe. Damage that is very mild may not need repairing, but severe lesions in cartilage and/or bone should preferably be covered to at least 90%.

In embodiments, the determining 580 of the final shape and dimensions of the customized implant suitable for repairing said determined damage comprises simulating a healthy surface at said proposed position, and designing the surface of the customized implant to match said simulated healthy surface. The healthy surface may e.g. be simulated based on the curvature of the cartilage surrounding the area of damaged cartilage, especially when the anatomical joint is a knee joint. However, the healthy surface may also be simulated based on the curvature of the bone surface surrounding the area of bone damage, especially when the determined damage is damage to the talus, where the damage to be repaired is generally bone damage.

In embodiments, the predefined set of implant templates comprises implants having implant hats that have a substantially circular shape in outline and implants having implant hats that are shaped to comprise at least two overlapping substantially circular shapes in outline.

In embodiments, the functionality to enable manipulation of the 3D model comprises functionality to select at least one medical image in the medical image stack to visualize through interaction with the 3D model, and functionality to, in the 3D model, visualize the position of at least one medical image that is currently visualized.

In some embodiments, the medical images are MR images, and each of the one or more medical image stacks has been generated during an MR scanning process using a specific MR sequence, wherein each specific MR sequence uses a unique set of MR parameters, in order to visualize different types of detail by visualizing different medical image stacks.

In other embodiments, the medical images are CT images, and each of the one or more medical image stacks has been generated during a CT scanning process using a specific CT sequence, wherein each specific CT sequence uses a unique set of CT parameters, in order to visualize different types of detail by visualizing different medical image stacks.

The generated 3D model may e.g. be visualized using a graphical user interface. The same, or a different, graphical user interface may also be used by personnel at a medical care facility, preferably the medical care facility where the medical imaging takes place, for uploading the medical image stacks into a storage media 110. Medical image stacks may however also be uploaded into the storage media 110 by another medical care facility, or by other authorized personnel. The uploading of the medical image stacks may also be an automatic uploading directly from one system to another.

Figure 6:
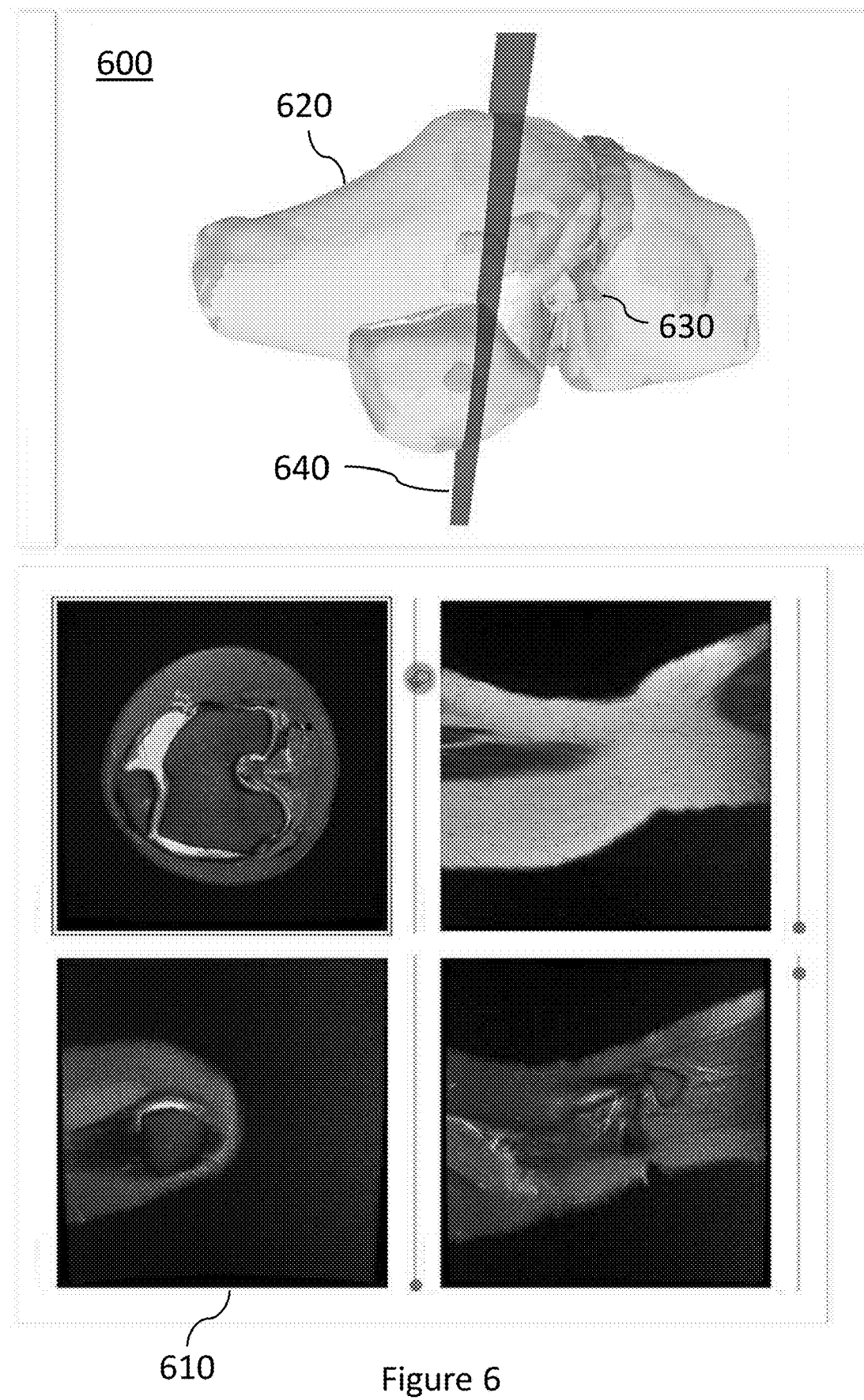
FIG. 6 shows an example of a graphical user interface for determining and visualizing damage to an anatomical joint, in accordance with one or more embodiments described herein.

FIG. 6 shows an example of a graphical user interface 600 comprising four displayed medical images 610 and a 3D model 620 in which determined damage 630 to an anatomical joint is visualized, in accordance with one or more embodiments described herein. The determined damage 630 may e.g. be visualized by changing the luminance/intensity levels and/or chrominance/color values of a number of pixels/voxels identified as being located on and surrounding the determined damage. Of course, any luminance/intensity values and/or chrominance/color values may be chosen, depending on the application, and depending on what provides a clear marking, visualization, or indication that enables a person viewing the graphical user interface to see and analyze the determined damage. A chosen luminance/intensity value and/or chrominance/color value may in embodiments be assigned to a pixel/voxel by replacing the previous pixel/voxel value, or by blending the new pixel/voxel values with the old pixel/voxel value using a scaling factor, such as an alpha blending factor. Determined damage may further be visualized using different assigned pixel/voxel values depending on the type of damage that each pixel represents. As an example, visualizing a damage may comprise different new pixel/voxel values for: a full-depth damage, i.e. a cartilage damage down to the bone; a partial depth damage, such as degenerated cartilage, regenerated cartilage/scar tissue, or deformed cartilage; a bone marrow lesion (BML); and a distinct cyst.

The graphical user interface may comprise functionality to visualize and enable manipulation, using at least one manipulation tool 150, of the at least one 3D model 620. The graphical user interface may further comprise functionality to visualize and enable browsing of at least one of the one or more medical image stacks. In the graphical user interface illustrated in FIG. 6, four image stacks are visualized. Below each of these image stacks, an indicator shows the position within the image stack of the image that is currently displayed. In the image to the top right in FIG. 6, the indicator shows that the user is browsing through the medical image stack. The position of the image in the medical image stack that is currently visualized, i.e. the intersection in the 3D model that is displayed in the medical image 610, is in FIG. 6 illustrated with a plane 640 through the 3D model. As the user browses through the medical images, the plane 640 moves in the 3D model 620.

FIG. 6 illustrates that the angle of such a plane 640 depends on the angle of the slices visualized in the images in the medical image stack, and the plane 640 may thus be at any angle through the 3D model. The user preferably has the option to remove the visualization of this plane 640, for increased clarity when viewing the 3D model.

The graphical user interface may further comprise functionality to enable removal of the visualization of at least one of the plurality of anatomical structures from the at least one 3D model. Anatomical structures such as e.g. femur, patella, cruciates, tibia, menisci and cartilage may be selectively added and removed from the visualization of the 3D model, e.g. using at least one manipulation tool 150. Through the functionality to add and remove the visualization of selected anatomical structures, the damage may be examined in much more detail than during an arthroscopy, since anatomical structures that are in the way can simply be removed from the visualization. This is especially powerful in combination with the functionality to manipulate the 3D model, so that it can be viewed from any angle, which greatly increases the overview of the damage in comparison with arthroscopy.

The graphical user interface may further comprise functionality to select at least one medical image 610 in the medical image stack to visualize through interaction with the 3D model 620, e.g. by manipulating the plane through the 3D model 620, using at least one manipulation tool 150.

In FIG. 6, a plurality of medical images 610 are shown. The plurality of medical images 610 may e.g. belong to different medical image stacks. In this way, the graphical user interface may comprise functionality to browse through a number of different medical image stacks.

In some embodiments, the graphical user interface may further include a recommendation and/or a position indication of a suitable implant for the determined bone and/or cartilage damage. Such a suitable implant may further be visualized in the 3D model and/or the displayed medical image. A decision support material may thus be generated for the physicians involved and ultimately to be distributed to the patient including visual representations of the damaged joint and of the corresponding implant.

Figure 7:
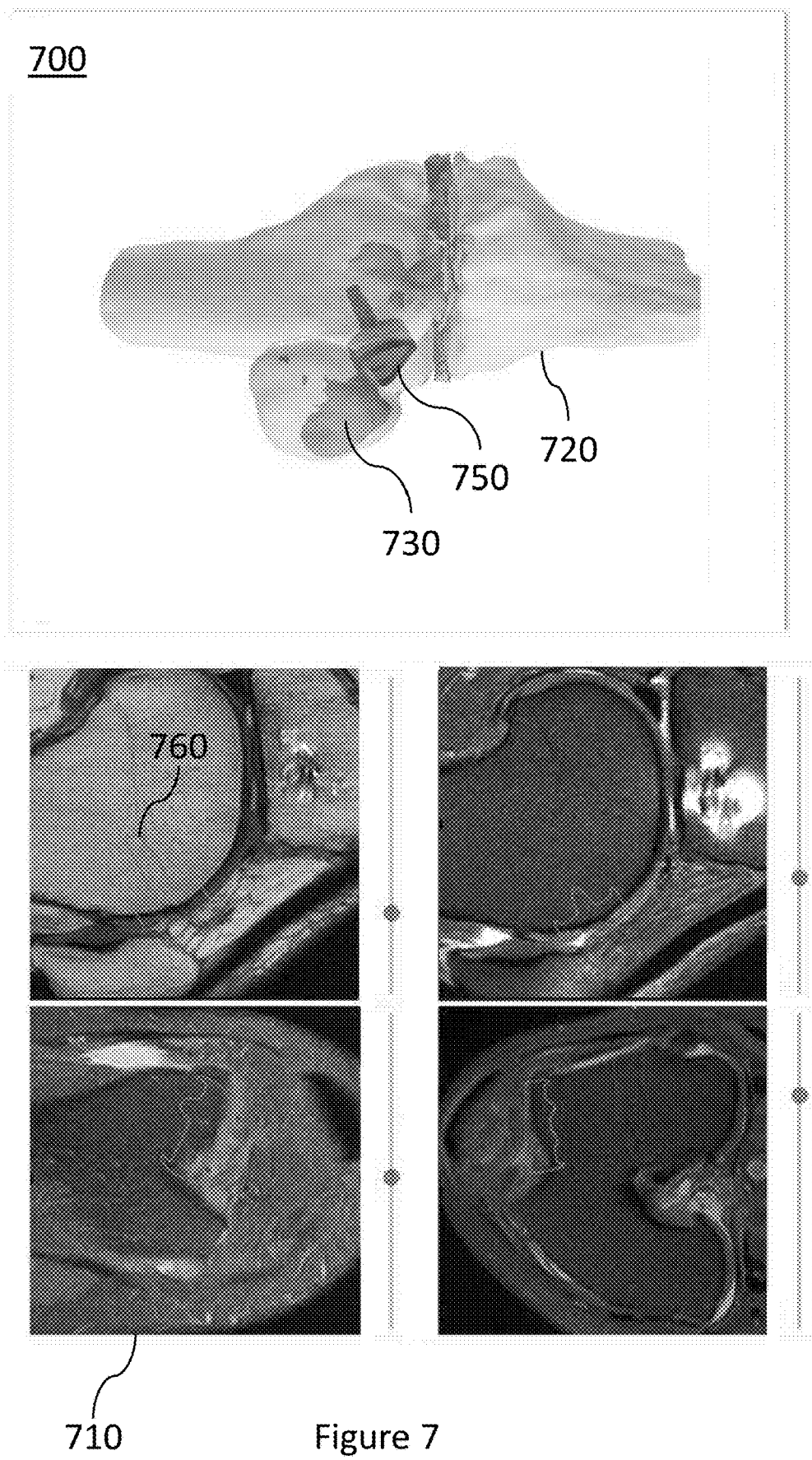
FIG. 7 shows an example of a graphical user interface for determining and visualizing damage to an anatomical joint, in accordance with one or more embodiments described herein.

An example of how or a type and placement of a suitable implant may be indicated in the graphical user interface 700 is shown in FIG. 7, which comprises four displayed medical images 710 and a 3D model 720 in which determined damage 730 to an anatomical joint is visualized. The type and placement of a suitable implant 750, 760 is in FIG. 7 indicated both in the medical image 710 and in the 3D model 720, but it may be indicated in just the 3D model 720.

In one or more embodiments, the graphical user interface may be manipulated by a user using at least one manipulation 150 tool integrated in, connected to, or communicatively coupled to a display 140 or a system 100 comprising a display 140. According to these embodiments, the method of FIG. 5 may further optionally comprise receiving user input from at least one manipulation tool 150, interpret the received user input, and generate one or more control signals in response to the received user input. The received user input may e.g. relate to the 3D model, and generate control signals in response to said received user input to manipulate what is being displayed, temporarily or permanently. The manipulation may for example include providing annotations, moving or changing an image or part of an image, changing the viewing perspective, zooming in or out, and/or any other suitable form of manipulation that enables the user to view and analyze the displayed image data in an improved manner. In some embodiments, the method of FIG. 5 may comprise receiving a control signal from at least one manipulation tool 150 and processing the image data that is being displayed, or in other words manipulate the displayed image, in response to the control signal.

Each of the medical image stacks used for determining damage to the identified tissue parts in the anatomical joint may be different from the medical image stack used for obtaining the three-dimensional image representation. In this way, the unique set of parameters used for generating each medical image stack can be optimized to the use of the medical image stack.

Any or all of the method steps of any or all of the embodiments presented herein may be performed automatically, e.g. by at least one processor.

Use Case Embodiment

Figure 8:
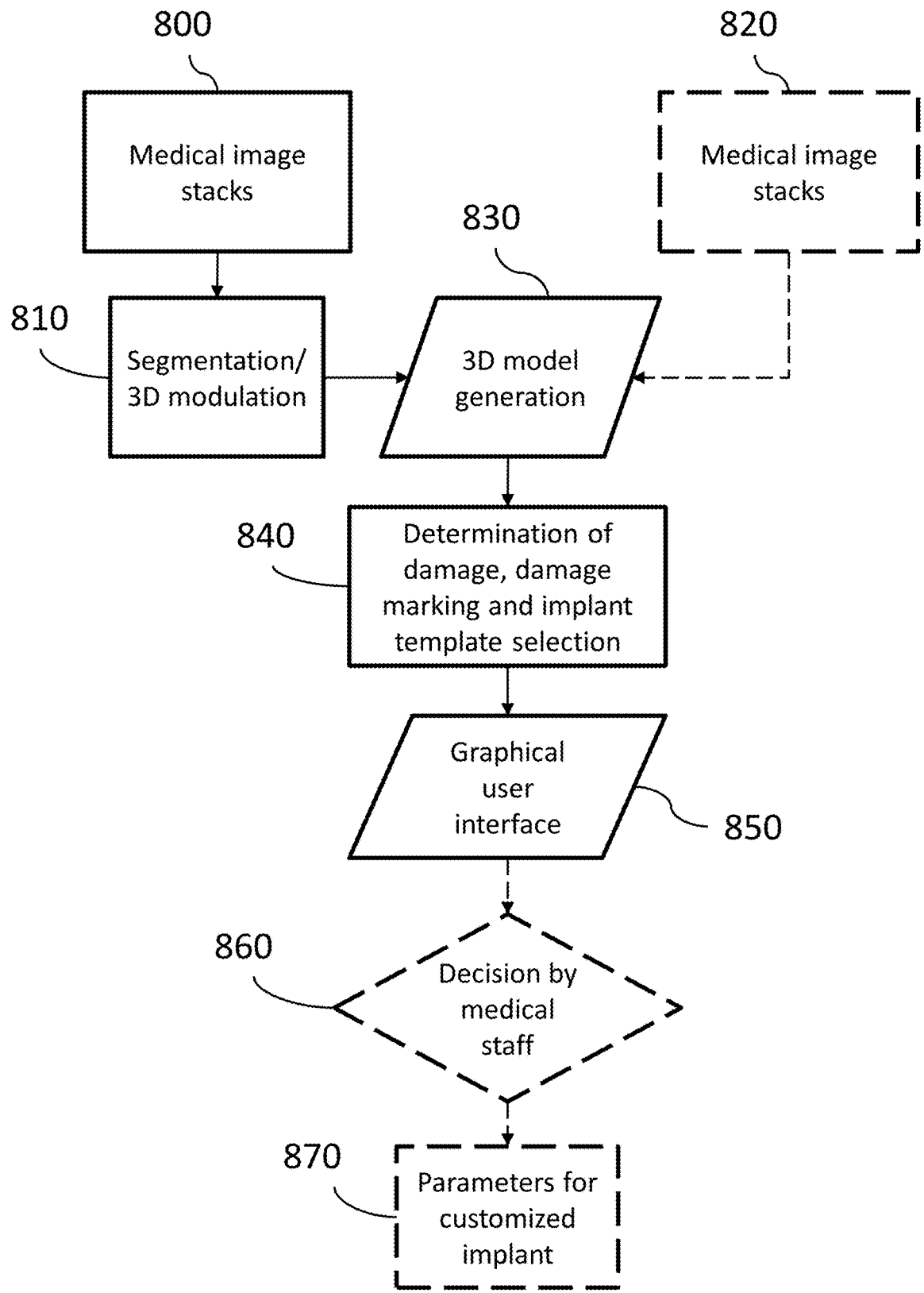
FIG. 8 is a flow diagram exemplifying the claimed method, including obtaining medical image stacks from an image source, determining damage to a depicted anatomical joint, and outputting final shape and dimensions of a customized implant suitable for repairing the determined damage as parameters for manufacturing said customized implant, in accordance with one or more embodiments described herein.

FIG. 8 is a flow diagram exemplifying the claimed method, including obtaining medical image stacks from an image source, determining damage to a depicted anatomical joint, and outputting final shape and dimensions of a customized implant suitable for repairing the determined damage as parameters for manufacturing said customized implant, in accordance with one or more embodiments described herein.

According to the example shown in FIG. 8, medical image stacks may be obtained in a step 800 in the form of medical image data from a medical imaging system 130. The medical image stacks obtained may for example be radiology data, generated using one or more of a variety of medical imaging techniques such as X-ray images, ultrasound images, computed tomography (CT) images, nuclear medicine including positron emission tomography (PET) images, and magnetic resonance imaging (MRI) images. The medical image stacks may e.g. be captured during a process of scanning images through different layers of the anatomical joint or part of it. In embodiments, the system comprises a storage media 110, into which the medical image stacks are uploaded by personnel at a medical care facility, preferably the medical care facility where the medical imaging takes place. Medical image stacks may however also be uploaded into the storage media 110 by another medical care facility, or by other authorized personnel. The uploading of the medical image stacks may also be an automatic uploading directly from one system to another.

In a step 830, a 3D model is generated based on at least one of the medical image stacks. The medical image stacks obtained in step 800 may be processed in a step 810, by performing segmentation and 3D modulation to obtain a three-dimensional image representation of what is depicted in the captured image data. For instance, if the image data captured depict an anatomical joint, the three-dimensional image representation would be a three-dimensional image representation of the anatomical joint. Medical image stacks may alternatively be obtained in a step 820 from a storage of medical image stacks, such as e.g. a storage media 110 into which the medical image stacks have been uploaded by personnel at a medical care facility, preferably the medical care facility where the medical imaging has taken place. Medical image stacks may however also be uploaded into the storage media 110 by another medical care facility, or by other authorized personnel. The uploading of the medical image stacks may also be an automatic uploading directly from one system to another. The medical image stacks depict the anatomical joint of interest for damage determination. The medical image stacks may represent only a part of the anatomical joint.

In a step 840, damage determination, marking of damage in the input medical image stacks, and selection of an implant template suitable for repairing the determined damage is performed, in accordance with any of the embodiments presented herein in connection with the method and system descriptions. A graphical user interface 850 may also be created, comprising functionality to visualize and enable manipulation, using at least one manipulation tool 150, of the 3D model. Such a graphical user interface may comprise functionality to select at least one medical image in the medical image stack to visualize through interaction with the 3D model; and functionality to visualize, in the 3D model, the position of the at least one medical image that is currently visualized. The graphical user interface 850 may, in accordance with embodiments described herein, comprise an indication of an implant template suitable for repairing the determined damage. In this context, a suitable implant template means an implant having a type and dimensions that match the determined damage, thereby making it suitable for repairing the determined damage. The implant template may be presented graphically in connection with the 3D model and/or the medical images of the graphical user interface 850, for example in the position where the implant should optimally be inserted to repair the determined damage.

In a use case embodiment, a medical staff member, for example a physician, e.g. a surgeon or an orthopedic staff member, may use the created graphical user interface 850 to visualize a proposed implant template and position for the patient whose anatomical joint has been depicted. If the medical staff member approves the proposal in step 860, this may lead up to the step 870 of outputting final shape and dimensions of a customized implant suitable for repairing the determined damage as parameters for manufacturing said customized implant.

There may be different users with different authorizations. Some users may be authorized only to upload images, some users may be authorized only to determine damage and/or propose an implant template and position, and some users may be authorized only to view the 3D model. Preferably, only one or more selected users, such as e.g. the physician, e.g. the surgeon, responsible for the patient, may submit an approval for the selected implant template in the proposed position. Thus, in embodiments, the approval is received from a user with a specific approval authorization, such as e.g. the physician responsible for the patient.

Further Embodiments

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the claimed scope of the present disclosure. Where applicable, the various hardware components and/or software components set forth herein can be separated into sub-components comprising software, hardware, or both without departing from the claimed scope of the present disclosure. In addition, where applicable, it is contemplated that software components can be implemented as hardware components, and vice-versa. The method steps of one or more embodiments described herein may be performed automatically, by any suitable processing unit, or one or more steps may be performed manually. Where applicable, the ordering of various steps described herein can be changed, combined into composite steps, and/or separated into sub-steps to provide features described herein.

Software in accordance with the present disclosure, such as program code and/or data, can be stored in non-transitory form on one or more machine-readable mediums. It is also contemplated that software identified herein can be implemented using one or more general purpose or specific purpose computers and/or computer systems, networked and/or otherwise.

In embodiments, there are provided a computer program product comprising computer readable code configured to, when executed in a processor, perform any or all of the method steps described herein. In some embodiments, there are provided a non-transitory computer readable memory on which is stored computer readable and computer executable code configured to, when executed in a processor, perform any or all of the method steps described herein.

In one or more embodiments, there is provided a non-transitory machine-readable medium on which is stored machine-readable code which, when executed by a processor, controls the processor to perform the method of any or all of the method embodiments presented herein.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

The invention claimed is:

1. A system for customizing an implant suitable for repairing damage in an anatomical joint of a patient, the system comprising a plurality of types of authorizations for different users and at least one processor configured to:
   i) obtain one or more medical image stacks of at least a part of the anatomical joint, wherein each of the medical image stacks are generated using a medical imaging system;
   ii) obtain a three-dimensional image representation of the at least part of the anatomical joint which is based on at least one of said medical image stacks;
   iii) determine damage to at least one of a plurality of anatomical structures in the anatomical joint by analyzing at least one of said one or more medical image stacks;
   iv) select an implant template to be used as a basis for a customized implant for repairing said determined damage from a predefined set of implant templates having predetermined types and sizes;
   v) generate a 3D model for visualization based on the three-dimensional image representation, in which 3D model marked damage is visualized together with the selected implant template in a proposed position;
   vi) display the 3D model with functionality to enable manipulation of the 3D model;
   vii) receive an approval for said selected implant template in said proposed position from a user having an approval authorization from the plurality of types of authorizations; and
   viii) determine the final shape and dimensions of a customized implant suitable for repairing said determined damage based on said selected implant template and said proposed position.

2. A system according to claim 1, wherein the system comprises a storage media, and the medical image stacks are obtained from said storage media, wherein the medical image stacks have been uploaded into said storage media by personnel at a medical care facility.

3. A system according to claim 1, wherein the plurality of anatomical structures are anatomical structures of the knee joint selected from the group comprising the femur, patella, tibia, fibula, cartilage, menisci, cruciate ligaments and tendons.

4. A system according to claim 1, wherein the proposed position of the selected implant template is a position where the selected implant template covers at least a major part of the determined damage, and a position that also minimizes at least one of the total volume of tissue to be removed for implanting the customized implant, or the surface area of the implant penetration into the bone.

5. A system according to claim 1, wherein the at least one processor is configured to determine the final shape and dimensions of the customized implant suitable for repairing said determined damage by simulating a healthy surface at said proposed position, including designing the surface of the customized implant to match said simulated healthy surface.

6. A system according to claim 5, wherein the healthy surface is simulated based on the curvature of the cartilage surrounding the area of damaged cartilage.

7. A system according to claim 1, wherein the predefined set of implant templates comprises implants having implant hats that have a substantially circular shape in outline and implants having implant hats that are shaped to comprise at least two overlapping substantially circular shapes in outline.

8. A system according to claim 1, wherein the functionality to enable manipulation of the 3D model comprises:
   functionality to select at least one medical image in the medical image stack to visualize through interaction with the 3D model; and
   functionality to, in the 3D model, visualize the position of at least one medical image that is currently visualized.

9. A system according to claim 1, wherein the at least one processor is further configured to output the final shape and dimensions of said customized implant as parameters for manufacturing said customized implant.

10. A method for customizing an implant suitable for repairing damage in an anatomical joint of a patient, the method comprising the steps of:
   i) obtaining one or more medical image stacks of at least a part of the anatomical joint, wherein each of the medical image stacks are generated using a medical imaging system;
   ii) obtaining a three-dimensional image representation of the at least part of the anatomical joint which is based on at least one of said medical image stacks;
   iii) determining damage to at least one of a plurality of anatomical structures in the anatomical joint by analyzing at least one of said one or more medical image stacks;
   iv) selecting an implant template to be used as a basis for a customized implant for repairing said determined damage from a predefined set of implant templates having predetermined types and sizes;
   v) generating a 3D model for visualization based on the three-dimensional image representation, in which 3D model marked damage is visualized together with the selected implant template in a proposed position;
   vi) displaying the 3D model with functionality to enable manipulation of the 3D model;
   vii) receiving an approval for said selected implant template in said proposed position from a user having an approval authorization from a plurality of types of authorizations for different users; and
   viii) determining the final shape and dimensions of a customized implant suitable for repairing said determined damage based on said selected implant template and said proposed position.

11. A method according to claim 10, further comprising uploading the medical image stacks into a storage media by personnel at a medical care facility, wherein the obtaining of the medical image stacks comprises obtaining the medical image stacks from said storage media.

12. A method according to claim 10, wherein the plurality of anatomical structures are anatomical structures of the knee joint selected from the group comprising the femur, patella, tibia, fibula, cartilage, menisci, cruciate ligaments and tendons.

13. A method according to claim 10, wherein the proposed position of the selected implant template is a position where the selected implant template covers at least a major part of the determined damage, and a position that also minimizes at least one of the total volume of tissue to be removed for implanting the customized implant, or the surface area of the implant penetration into the bone.

14. A method according claim 10, wherein the determining of the final shape and dimensions of the customized implant suitable for repairing said determined damage comprises simulating a healthy surface at said proposed position, including designing the surface of the customized implant to match said simulated healthy surface.

15. A method according to claim 14, wherein the healthy surface is simulated based on the curvature of the cartilage surrounding the area of damaged cartilage.

16. A method according to claim 10, wherein the predefined set of implant templates comprises implants having implant hats that have a substantially circular shape in outline and implants having implant hats that are shaped to comprise at least two overlapping substantially circular shapes in outline.

17. A method according to claim 10, wherein the functionality to enable manipulation of the 3D model comprises:
   functionality to select at least one medical image in the medical image stack to visualize through interaction with the 3D model; and
   functionality to, in the 3D model, visualize the position of at least one medical image that is currently visualized.

18. A method according to claim 10, further comprising outputting the final shape and dimensions of said customized implant as parameters for manufacturing said customized implant.

19. A customized implant suitable for repairing damage in an anatomical joint of a patient, wherein the implant has been manufactured using the manufacturing parameters output according to claim 18.

20. A non-transitory machine-readable medium on which is stored machine-readable code which, when executed by at least one processor, controls the processor to perform the method of claim 10.

* * * * *